US006214538B1

(12) United States Patent
Jackwood et al.

(10) Patent No.: US 6,214,538 B1
(45) Date of Patent: Apr. 10, 2001

(54) DIFFERENTIATION OF AVIAN INFECTIOUS BRONCHITIS VIRUS SEROTYPES

(75) Inventors: Mark W. Jackwood, Watkinsville; Hyuk Moo Kwon, Athens, both of GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 07/922,492

(22) Filed: Jul. 30, 1992

(51) Int. Cl.[7] .............................. C12Q 1/68; C12Q 1/70; C07H 21/04
(52) U.S. Cl. .................. 435/5; 435/6; 536/23.1; 536/24.33
(58) Field of Search ...................... 435/5, 91, 6; 536/27, 536/23.1, 24.33

(56) References Cited

PUBLICATIONS

Binns et al., J. Gen. Virol. 66:719–726 (1985).
Binns et al., J. Gen. Virol. 67:2825–2831 (1986).
Cavanagh, J., J. Gen. Virol. 64:1787–1791 (1983).
Clewley et al., Infect. Immun. 32:1277–1233 (1981).
Gelb, J. Jr., et al., Avian Dis. 25:655–666 (1981).
Gelb, J. Jr., et al., Avian DIs. 35:82–87 (1991).
King and Hopkins, Avian Dis. 28:727–733 (1984).
King, D. J., Avian Dis. 32:362–364 (1988).
Koch et al., Isr. J. Vet. Med.42:89–97 (1986).
Koch et al., J. Gen. Virol. 71:1929–1935 (1990).
Kusters et al., Virology. 169:217–221 (1989).
Holmes, K. V. Chapter 18, Coronaviridae and Their Replication. Fundamental Virology 2nd Ed. 471–481 (1991).
Lin et al., Arch. Virol. 116:19–31 (1991).
Lin et al., Arch. Virol. 120:145–149 (1991).
Siddle et al., Curr. Top. Microbiol. Immunol. 99:131–163 (1982).

*Primary Examiner*—David Guzo
(74) *Attorney, Agent, or Firm*—Needle & Rosenberg, PC

(57) ABSTRACT

The present invention relates, in general, to the genetics of viruses. In particular, the present invention provides methods of distinguishing between serotypes of avian infectious bronchitis virus based on restriction fragment length polymorphisms derived from the region of the S1 gene of IBV, peptides derived from the restriction fragments, related primers for polymerase chain reaction, and certain restriction length polymorphism patterns.

5 Claims, 5 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:1:

CCANNNNNNN NNTGG                                                      15

(2) INFORMATION FOR SEQ ID NO:2:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

RGATCY                                                                 6

(2) INFORMATION FOR SEQ ID NO:3:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GATTTGAGAT TGAAAGCAAC GCCAGTTGTT AATTTGAAAA CTGAACAAAA GACAGACTTA      60

GTCTTTAATT TAATTAAGTG TGGTAAGTTA CTGGTAAGAG A                         101

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TGAAAACTGA ACAAAAGACA                                                  20

(2) INFORMATION FOR SEQ ID NO:5:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGTTTTAGAC GTTCTATTAC TGAAAATGTT GCAAATTGCC CTTATGTTAG TTATGGTAAG      60

TTTTGTATAA AACCTGATGG CTCAATTGCC ACAATAGTAC C                         101

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CATAACTAAC ATAAGGGCAA                                                    20

(2) INFORMATION FOR SEQ ID NO:7:

(i) SEQUENCE CHARACTERISTICS:
        (A) LENGTH: 1720 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGAAAACTGA ACAAAAGACA GACTTAGTCT TTAATTTAAT TAAGTGTGGT AAGTTACTGG        60

TAAGAGATGT TGGTAACACC TCTTTTACTA GTGACTCTTT TGTGTGCACT ATGTAGTGCT       120

GTTTTGTATG ACAGTAGTTC TTACGTTTAC TACTACCAAA GTGCCTTCAG ACCACCTAGT       180

GGTTGGCATT TACAAGGGGG TGCTTATGCG GTAGTTAACA TTTCTAGCGA ATTTAATAAT       240

GCAGGCTCTT CATCAGGGTG TACTGTTGGT ATTATTCATG GTGGTCGTGT TGTTAATGCT       300

TCTTCTATAG CTATGACGGC ACCGTCATCA GGTATGGCTT GGTCTAGCAG TCAGTTTTGT       360

ACTGCACACT GTAATTTTTC AGATACTACA GTGTTTGTTA CACATTGTTA TAAACATGGT       420

GGGTGTCCTT TAACTGGCAT GCTTCAACAG AATCTTATAC GTGTTTCTGC TATGAAAAAT       480

GGCCAGCTTT TCTATAATTT AACAGTTAGT GTAGCTAAGT ACCCTACTTT TAGATCATTT       540

CAGTGTGTTA ATAATTTAAC ATCCGTATAT TTAAATGGTG ATCTTGTTTA CACCTCTAAT       600

GAGACCATAG ATGTTACATC TGCAGGTGTT TATTTTAAAG CTGGTGGACC TATAACTTAT       660

AAAGTTATGA GAGAAGTTAA AGCCCTGGCT TATTTTGTTA ATGGTACTGC ACAAGATGTT       720

ATTTTGTGTG ATGGATCACC TAGAGGCTTG TTAGCATGCC AGTATAATAC TGGCAATTTT       780

TCAGATGGCT TTTATCCTTT TACTAATAGT AGTTTAGTTA AGCAGAAGTT TATTGTCTAT       840

CGTGAAAATA GTGTTAATAC TACTTGTACG TTACACAATT TCATTTTTCA TAATGAGACT       900

GGCGCCAACC CTAATCCTAG TGGTGTTCAG AATATTCAAA CTTACCAAAC AAAAACAGCT       960

CAGAGTGGTT ATTATAATTT TAATTTTTCC TTTCTGAGTA GTTTTGTTTA TAAGGAGTCT      1020

AATTTTATGT ATGGATCTTA TCACCCAAGT TGTAAATTTA GACTAGAAAC TATTAATAAT      1080

GGCTTGTGGT TTAATTCACT TTCAGTTTCA ATTGCTTACG GTCCTCTTCA AGGTGGTTGC      1140

AAGCAATCTG TCTTTAAAGG TAGAGCAACT TGTTGTTATG CTTATTCATA TGGAGGTCCT      1200

TCGCTGTGTA AAGGTGTTTA TTCAGGTGAG TTAGATCATA ATTTTGAATG TGGACTGTTA      1260

GTTTATGTTA CTAAGAGCGG TGGCTCTCGT ATACAAACAG CCACTGAACC GCCAGTTATA      1320

ACTCAAAACA ATTATAATAA TATTACTTTA AATACTTGTG TTGATTATAA TATATATGGC      1380

AGAACTGGCC AAGGTTTTAT TACTAATGTG ACCGACTCAG CTGTTAGTTA TAATTATCTA      1440

GCAGACGCAG GTTTGGCTAT TTTAGATACA TCTGGTTCCA TAGACATCTT TGTTGTACAA      1500

GGTGAATATG GTCTTAATTA TTATAAGGTT AACCCTTGCG AAGATGTCAA CCAGCAGTTT      1560

GTAGTTTCTG GTGGTAAATT AGTAGGTATT CTTACTTCAC GTAATGAGAC TGGTTCTCAG      1620

```
CTTCTTGAGA ACCAGTTTTA CATCAAAATC ACTAATGGAA CACGTCGTTT TAGACGTTCT    1680

ATTACTGAAA ATGTTGCAAA TTGCCCTTAT GTTAGTTATG                          1720
```

DIFFERENTIATION OF AVIAN INFECTIOUS BRONCHITIS VIRUS SEROTYPES

This invention was made with government support by the Veterinary Medical Experiment Station, University of Georgia (Project #29-26-GR207). The U.S. Government may have certain rights in this invention.

FIELD OF THE INVENTION

The present invention relates, in general, to the genetics of viruses. In particular, the present invention relates to methods of distinguishing between serotypes of avian infectious bronchitis virus based on restriction fragment length polymorphisms, peptides derived from the restriction fragments, related primers for polymerase chain reaction, and certain restriction fragment length polymorphism patterns.

BACKGROUND INFORMATION

Infectious bronchitis virus (IBV), the prototype of the family Coronaviridae, is the etiological agent of infectious bronchitis (IB), an acute, highly contagious disease of the respiratory and urogenital tracts of chickens (21). In spite of the use of vaccines for the control of IB, the disease continues to be a problem in commercial poultry because some serotypes do not cross protect against antigenically unrelated serotypes including variant strains of the virus (12,20).

Both the isolation and serotype identification of IBV field isolates are important because vaccines are selected based on the serotypes of field isolates in a given area. Identification of newly introduced IBV serotypes or variant strains of IBV in a geographical area can be used to modify vaccination programs in order to provide greater protection against the endemic serotypes.

Traditionally, IBV serotypes are identified by the virus neutralization (VN) test, or by the hemagglutination-inhibition (HI) test (9,11,19). Other methods such as, monoclonal antibodies (22), and oligonucleotide fingerprinting (6) have also been used to determine the serotype of IBV isolates. Traditional methods for identifying IBV serotypes are labor intensive and time-consuming. In addition, the use of antibodies, which is somewhat less labor-intensive, cannot detect variants.

IBV contains three structural proteins; the spike (S) glycoprotein, the membrane glycoprotein, and the nucleocapsid protein (30). The S glycoprotein comprises two glycopolypeptides, S1 and S2 (4). Neutralizing and serotype specific antibodies are directed against the S1 glycoprotein (5,23). Thus, unique epitopes on that glycoprotein determine serotype, and are reflected in the gene that codes for the S1 glycoprotein.

IBV has multiple serotypes and new variant serotypes continue to be recognized. When designing a vaccination program for IBV, it is important to identify the serotype of field strains since there may be limited cross-protection between different serotypes of the virus. Although several methods (6,7,16,22) have been used to group IBV isolates, those methods are time consuming and have produced conflicting results. The VN test is the traditional method of serotyping IBV isolates. Thus, any new method must agree with the results of the VN test to be of practical value.

It is well known that neutralizing and serotype specific epitopes are located on the S1 glycoprotein of IBV, but their exact location is not known (5,23).

Lin et al. (26,27) used a polymerase chain reaction-restriction fragment length polymorphism (PCR-RFLP) method for grouping IBV isolates. In that study, they amplified 400 bases of the N terminal region of the S2 glycoprotein gene, and categorized 12 IBV strains into several groups. In addition, the data set forth in Lin et al. does not adequately support distinguishing serotypes of IBV. That method required 9 different restriction endonuclease (RE) and utilized restriction fragment length polymorphism (RFLP) analysis as well as complicated RE digestion profiles. Thus, despite a great need for a simple and efficient method to distinguish serotypes, Lin et al. fell far short with this inadequate and complicated RE procedure. Further, the utility of that analysis was not verified with additional IBV isolates.

Thus, despite the efforts of many, there remains a great need for a simple, accurate method to distinguish IBV serotypes. The present invention satisfies this need by providing three restriction enzymes which, when used to cleave amplified S1 gene regions, are individually able to distinguish many serotypes of IBV. Further, when separately used on a test sample, the three restriction enzymes were able to distinguish virtually all available serotypes.

SUMMARY OF THE INVENTION

In one embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with HaeIII, or a restriction endonuclease which cleaves at the HaeIII restriction site, to form restriction fragments;

c) separating the restriction fragment length polymorphisms by electrophoresis; and d) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with XcmI, or a restriction endonuclease which cleaves at the XcmI restriction site, to form restriction fragments;

c) separating the restriction fragments by electrophoresis; and d) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with BstYI, or a restriction endonuclease which cleaves at the BstYI restriction site, to form restriction fragments;

c) separating the restriction fragments by electrophoresis; and d) analyzing restriction fragment length polymorphisms to distinguish between serotypes or detect variants of infectious bronchitis virus.

In a further embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with HaeIII, or a restriction endonuclease which cleaves at the HaeIII restriction site, to form a first set of restriction fragments;

c) separately digesting the amplified S1 gene region with XcmI, or a restriction endonuclease which cleaves at the XcmI restriction site, to form a second set of restriction fragments;

d) separating the restriction fragments within the first and second sets by electrophoresis; and e) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with HaeIII, or a restriction endonuclease which cleaves at the HaeIII restriction site, to form a first set of restriction fragments;

c) separately digesting the amplified S1 gene region with BstYI, or a restriction endonuclease which cleaves at the BstYI restriction site, to form a second set of restriction fragments;

d) separating the restriction fragments within the first and second sets by electrophoresis; and e) analyzing restriction fragment length polymorphisms to distinguish between serotypes or detect variants of infectious bronchitis virus.

Another embodiment of the present invention is a method of distinguishing between serotypes and/or detecting variants of infectious bronchitis virus comprising:

a) amplifying the S1 gene region of infectious bronchitis virus;

b) digesting the amplified S1 gene region with XcmI, or a restriction endonuclease which cleaves at the XcmI restriction site, to form a first set of restriction fragments;

c) digesting the amplified S1 gene region with BstYI, or a restriction endonuclease which cleaves at the BstYI restriction site, to form a second set of restriction fragments;

d) separating the restriction fragments within the first and second sets by electrophoresis; and e) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with HaeIII, or a restriction endonuclease which cleaves at the HaeIII restriction site, to form a first set of restriction fragments;

c) digesting the amplified S1 gene region with XcmI, or a restriction endonuclease which cleaves at the XcmI restriction site, to form a second set of restriction fragments;

d) digesting the amplified S1 gene region with BstYI, or restriction endonuclease which cleaves at the BstYI restriction site, to form a third set of restriction fragments;

e) separating the restriction fragments within the first, second and third sets by electrophoresis; and f) analyzing restriction fragment length polymorphisms to distinguish between serotypes or detect variants of infectious bronchitis virus.

In a further embodiment, this invention provides a primer for amplifying the S1 gene region of infectious bronchitis virus comprising a nucleic acid, having at least 20 nucleotides, which selectively hybridizes between nucleotide positions −100 through +1 (relative to the ATG start site of S1) of the negative strand of infectious bronchitis virus.

In another embodiment, this invention provides a primer for amplifying the S1 gene region of infectious bronchitis virus comprising a nucleic acid, having at least 20 nucleotides, which selectively hybridizes between nucleotide positions 1600 through 1700 (relative to the ATG start site of S1) of the positive strand of infectious bronchitis virus.

In another embodiment, the present invention provides a method of detecting the presence of a serotype of infectious bronchitis virus comprising ascertaining the presence of a nucleotide sequence associated with a restriction endonuclease cleavage site, created by digestion with HaeIII and/or XcmI and/or BstYI, by hybridizing the sequence with a selective nucleic acid probe.

In another embodiment, the present invention provides a method of detecting the presence of a serotype of infectious bronchitis virus comprising ascertaining the presence of a nucleotide sequence associated with a restriction endonuclease cleavage site, created by digestion with HaeIII and/or XcmI and/or BstYI, by selective amplification.

In another embodiment, the present invention provides a method of detecting the presence of a serotype of infectious bronchitis virus comprising ascertaining the presence of a nucleotide sequence associated with a restriction endonuclease cleavage site, created by digestion with HaeIII and/or XcmI and/or BstYI, by determining the order of nucleotides by sequencing.

Another separate embodiment of this invention provides a polypeptide portion of the S1 protein of infectious bronchitis virus comprising the amino acids encoded by the nucleotide sequence associated with the HaeIII and/or XcmI and/or BstYI restriction site.

In another embodiment, this invention provides the restriction length polymorphism patterns for the IBV strains respectively shown in FIGS. 2–5.

DETAILED DESCRIPTION OF THE INVENTION

Figure 1:
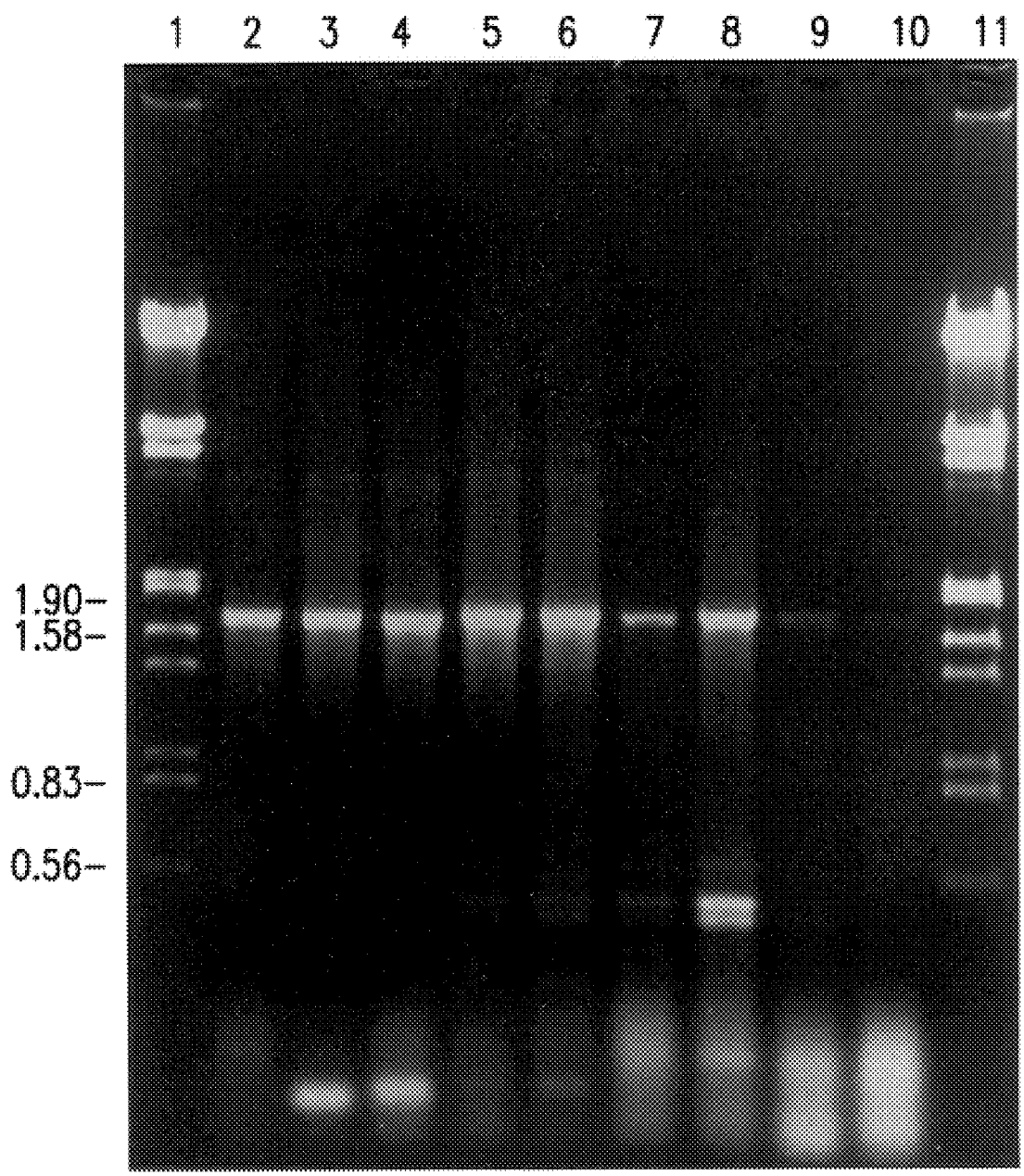
FIG. 1 shows agarose gel electrophoresis of PCR amplified products of single-stranded cDNA made from RNA extracted from several infectious bronchitis virus strains. Lane 1 and lane 11: molecular size marker bacteriophage lambda DNA digested with HindIII and EcoRI; lane 2: Beaudette; lane 3: Connecticut; lane 4: Florida 88; lane 5: Gray; lane 6: JMK; lane 7: Holte; lane 8: Arkansas DPI; lane 9: SE 17; lane 10: Iowa 97. Numbers on the vertical axis represent sizes in kilobase pairs of molecular size markers.

In one embodiment, the present invention provides a method of distinguishing between serotypes and/or detecting variants of infectious bronchitis virus comprising:
 a) amplifying the S1 gene region of infectious bronchitis virus;
 b) digesting the amplified S1 gene region with HaeIII, or a restriction endonuclease which cleaves at the HaeIII restriction site, to form restriction fragments;
 c) separating the restriction fragment length polymorphisms by electrophoresis; and
 d) analyzing restriction fragment length polymorphisms to distinguish between serotypes or detect variants of infectious bronchitis virus.

As used in this invention:

"Variant" means a genetically distinct strain of IBV which can be classified under one of the known serotypes.

"S1 gene region" means the region of S1 containing restriction sites for the HaeIII, XcmI, and BstYI (or equivalent) restriction endonucleases. In one embodiment described in more detail below, the S1 gene region is the approximately 1720 base pair region of IBV RNA which encodes the S1 glycopolypeptide, i.e. the region amplified by primers S10LIG03' and S10LIG05'. However, so long as the restriction site or sites are amplified, the invention will work.

It will be recognized by the skilled artisan that any method which can amplify the region containing the restriction sites will be effective. Thus, "amplification" can include, but is not limited to, the following methods: polymerase chain reaction, ligase chain reaction, or QB-RNA replication (37). However, polymerase chain reaction is the currently preferred means of amplification.

The HaeIII restriction site is 5'-GG$^1$CC-3'. The XcmI restriction site is 5'-CCANNNNN$^1$NNNNTGG-3' [SEQ ID NO:1] where N represents any base. The BstYI restriction site is 5'-R$^1$GATCY-3' [SEQ ID NO:2] where R represents any purine, and Y represents any pyramidine. Therefore, one skilled in the art will recognize that other restriction endonucleases, whether now known or later discovered, could cleave in equivalent positions.

In another embodiment, the present invention provides a method of distinguishing between serotypes and/or detecting variants of infectious bronchitis virus comprising:
 a) amplifying the S1 gene region of infectious bronchitis virus;
 b) digesting the amplified S1 gene region with XcmI, or a restriction endonuclease which cleaves at the XcmI restriction site, to form restriction fragments;
 c) separating the restriction fragments by electrophoresis; and
 d) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:
 a) amplifying the S1 gene region of infectious bronchitis virus;
 b) digesting the amplified S1 gene region with BstYI, or a restriction endonuclease which cleaves at the BstYI restriction site, to form restriction fragments;
 c) separating the restriction fragments by electrophoresis; and
 d) analyzing restriction fragment length polymorphisms to distinguish between serotypes or detect variants of infectious bronchitis virus.

In a further embodiment, the present invention provides a method of distinguishing between serotypes and/or detecting variants of infectious bronchitis virus comprising:
 a) amplifying the S1 gene region of infectious bronchitis virus;
 b) digesting the amplified S1 gene region with HaeIII, or a restriction endonuclease which cleaves at the HaeIII restriction site, to form a first set of restriction fragments;
 c) separately digesting the amplified S1 gene region with XcmI, or a restriction endonuclease which cleaves at the XcmI restriction site, to form a second set of restriction fragments;
 d) separating the restriction fragments within the first and second sets by electrophoresis; and
 e) analyzing restriction fragment length polymorphisms to distinguish between serotypes or detect variants of infectious bronchitis virus.

In another embodiment, the present invention provides a method of distinguishing between serotypes and/or detecting variants of infectious bronchitis virus comprising:
 a) amplifying the S1 gene region of infectious bronchitis virus;
 b) digesting the amplified S1 gene region with HaeIII, or a restriction endonuclease which cleaves at the HaeIII restriction site, to form a first set of restriction fragments;

c) separately digesting the amplified S1 gene region with BstYI, or a restriction endonuclease which cleaves at the BstYI restriction site, to form a second set of restriction fragments;

d) separating the restriction fragments within the first and second sets by electrophoresis; and e) analyzing restriction fragment length polymorphisms to distinguish between serotypes or detect variants of infectious bronchitis virus.

Another embodiment of the present invention is a method of distinguishing between serotypes and/or detecting variants of infectious bronchitis virus comprising:

a) amplifying the S1 gene region of infectious bronchitis virus;

b) digesting the amplified S1 gene region with XcmI, or a restriction endonuclease which cleaves at the XcmI restriction site, to form a first set of restriction fragments;

c) digesting the amplified S1 gene region with BstYI, or a restriction endonuclease which cleaves at the BstYI restriction site, to form a second set of restriction fragments;

d) separating the restriction fragments within the first and second sets by electrophoresis; and e) analyzing restriction fragment length polymorphisms to distinguish between serotypes or detect variants of infectious bronchitis virus.

In a preferred embodiment, the present invention provides a method of distinguishing between serotypes and/or detecting variants of infectious bronchitis virus comprising:

a) amplifying the S1 gene region of infectious bronchitis virus;

b) digesting the amplified S1 gene region with HaeIII, or a restriction endonuclease which cleaves at the HaeIII restriction site, to form a first set of restriction fragments;

c) digesting the amplified S1 gene region with XcmI, or a restriction endonuclease which cleaves at the XcmI restriction site, to form a second set of restriction fragments;

d) digesting the amplified S1 gene region with BstYI, or a restriction endonuclease which cleaves at the BstYI restriction site, to form a third set of restriction fragments;

e) separating the restriction fragments within the first, second and third sets by electrophoresis; and f) analyzing restriction fragment length polymorphisms to distinguish between serotypes or detect variants of infectious bronchitis virus. This method as described in detail in the Experimental section allows one to distinguish virtually all serotypes tested.

In a further embodiment, this invention provides a primer for amplifying the S1 gene region of infectious bronchitis virus comprising a nucleic acid, having at least 20 nucleotides, which selectively hybridizes between nucleotide positions −100 through +1 of the negative strand of infectious bronchitis virus relative to the ATG start site of S1. The sequence the primer is selected from is 5'-GATTTGAGATTGAAAGCAACGCCAGTTGTTAATT TGAAAACTGAACAAAAGACAGACTTAGT CTTTAAT TTAATTAAGTGTGGTAAGTTACTGGTAAGAGA-3' [SEQ ID NO:3] (of the positive strand). (The primer sequence is underlined.) One such primer is 5'-TGAAAACTGAACAAAAGACA-3' [SEQ ID NO:4] (also referred to herein as S10LIG05').

In another embodiment, this invention provides a primer for amplifying the S1 gene region of infectious bronchitis virus comprising a nucleic acid, having at least 20 nucleotides, which selectively hybridizes between nucleotide positions 1600 through 1700 of the positive strand of infectious bronchitis virus relative to the ATG start site of S1. The sequence which the primer hybridizes is 5'-CGTTTTAGACGTTCTATTACTGAAAATGTTGCAAA TTGCCCTTATGTTAGTTATGGTAAGTTTTGTATAA AACCTGATGGCTCAATTGCCACAATAGTACC-3' [SEQ ID NO:5] (of the positive strand). (The primer sequence is underlined.) This primer could be 5'-CATAACTAACATAAGGGCAA-3' [SEQ ID NO:6] (also referred to herein as S10LIG03').

Based on the success of SEQ ID NO:4 and SEQ ID NO:6, one would predict these surrounding nucleotides could serve as a template for hybridization. This is true because these regions are sufficiently close to SEQ ID NO:3 and SEQ ID NO:4 to assure amplification of the relevant XcmI, BstYI and HaeIII restriction sites. In addition, since the specific relevant region has been identified, one would merely need to make an alternative primer to this region, run the primer on the PCGENE program (IntelliGenetics, Inc., Mountain View, Calif.) to determine if there would be prohibitive hybridization between the primers, hybridization with other regions of IBV, or self hybridization. If the primer is a successful candidate, the primer can be used to amplify as described in the examples and RFLPs analyzed. The entire sequence for IBV Beaudette strain is published and can be utilized to determine the unwanted hybridization (39–45).

Based on the present discovery, one can utilize the known nucleotide sequences for S1 to determine the precise location(s) of cleavage. This is accomplished by simply reviewing the known S1 sequences for the location of the HaeIII, XcmI and BstYI restriction sites. Once these sites are located and associated with a particular serotype, one can use many well-known methods, in addition to RFLPs, to directly determine the presence of the serotype.

Thus, the PCR product amplified by the SEQ ID NO:4 (S10LIG05') and SEQ ID NO:6 (S10LIG03') primers based on the published sequence for the Beaudette strain of IBV would be:

TGAAAACTGA ACAAAAGACA GACTTAGTCT
TTAATTTAAT TAAGTGTGGT AAGTTACTGG
TAAGAGATGT TGGTAACACC TCTTTTACTA
GTGACTCTTT TGTGTGCACT ATGTAGTGCT
GTTTTGTATG ACAGTAGTTC TTACGTTTAC
TACTACCAAA GTGCCTTCAG ACCACCTAGT
GGTTGGCATT TACAAGGGGG TGCTTATGCG
GTAGTTAACA TTTCTAGCGA ATTTAATAAT
GCAGGCTCTT CATCAGGGTG TACTGTTGGT
ATTATTCATG GTGGTCGTGT TGTTAATGCT TCT-
TCTATAG CTATGACGGC ACCGTCATCA
GGTATGGCTT GGTCTAGCAG TCAGTTTTGT
ACTGCACACT GTAATTTTTC AGATACTACA
GTGTTTGTTA CACATTGTTA TAAACATGGT
GGGTGTCCTT TAACTGGCAT GCTTCAACAG
AATCTTATAC GTGTTTCTGC TATGAAAAAT
GGCCAGCTTT TCTATAATTT AACAGTTAGT
GTAGCTAAGT ACCCTACTTT TAGATCATTT
CAGTGTGTTA ATAATTTAAC ATCCGTATAT
TTAAATGGTG ATCTTGTTTA CACCTCTAAT
GAGACCATAG ATGTTACATC TGCAGGTGTT
TATTTTAAAG CTGGTGGACC TATAACTTAT
AAAGTTATGA GAGAAGTTAA AGCCCTGGCT
TATTTTGTTA ATGGTACTGC ACAAGATGTT
ATTTTGTGTG ATGGATCACC TAGAGGCTTG
TTAGCATGCC AGTATAATAC TGGCAATTTT
TCAGATGGCT TTTATCCTTT TACTAATAGT
AGTTTAGTTA AGCAGAAGTT TATTGTCTAT

CGTGAAAATA GTGTTAATAC TACTTGTACG
TTACACAATT TCATTTTTCA TAATGAGACT
GGCGCCAACC CTAATCCTAG TGGTGTTCAG
AATATTCAAA CTTACCAAAC AAAAACAGCT
CAGAGTGGTT ATTATAATTT TAATTTTTCC
TTTCTGAGTA GTTTTGTTTA TAAGGAGTCT
AATTTTATGT ATGGATCTTA TCACCCAAGT
TGTAAATTTA GACTAGAAAC TATTAATAAT
GGCTTGTGGT TTAATTCACT TTCAGTTTCA
ATTGCTTACG GTCCTCTTCA AGGTGGTTGC
AAGCAATCTG TCTTTAAAGG TAGAGCAACT
TGTTGTTATG CTTATTCATA TGGAGGTCCT
TCGCTGTGTA AAGGTGTTTA TTCAGGTGAG
TTAGATCATA ATTTTGAATG TGGACTGTTA
GTTTATGTTA CTAAGAGCGG TGGCTCTCGT
ATACAAACAG CCACTGAACC GCCAGTTATA
ACTCAAAACA ATTATAATAA TATTACTTTA
AATACTTGTG TTGATTATAA TATATATGGC
AGAACTGGCC AAGGTTTTAT TACTAATGTG
ACCGACTCAG CTGTTAGTTA TAATTATCTA
GCAGACGCAG GTTTGGCTAT TTTAGATACA
TCTGGTTCCA TAGACATCTT TGTTGTACAA
GGTGAATATG GTCTTAATTA TTATAAGGTT
AACCCTTGCG AAGATGTCAA CCAGCAGTTT
GTAGTTTCTG GTGGTAAATT AGTAGGTATT
CTTACTTCAC GTAATGAGAC TGGTTCTCAG
CTTCTTGAGA ACCAGTTTTA CATCAAAATC
ACTAATGGAA CACGTCGTTT TAGACGTTCT
ATTACTGAAA ATGTTGCAAA TTGCCCTTAT
GTTAGTTATG [SEQ ID NO:7]

Thus, in another embodiment, the present invention provides a method of detecting the presence of a serotype of infectious bronchitis virus comprising ascertaining the presence of a nucleotide sequence associated with a restriction endonuclease cleavage site, created by digestion with HaeIII, by hybridizing the sequence with a selective nucleic acid probe. In one method, DNA can be loaded onto filters using the alkaline dot blot procedure (36). This method may be facilitated by amplification of the nucleotide sequence prior to hybridization as described herein or elsewhere (37).

In another embodiment, the present invention provides a method of detecting the presence of a serotype of infectious bronchitis virus comprising ascertaining the presence of a nucleotide sequence associated with a restriction endonuclease cleavage site, created by digestion with HaeIII, by selective amplification. For example, PCR primers which hybridize only with a specific serotype could be utilized. The presence of amplification indicates the presence of the serotype.

In another embodiment, the present invention provides a method of detecting the presence of a serotype of infectious bronchitis virus comprising ascertaining the presence of a nucleotide sequence associated with a restriction endonuclease cleavage site, created by digestion with HaeIII, by determining the order of nucleotides by sequencing. The DNA can be sequenced directly using Sanger ddNTp sequencing or 7-deaza-2'-deoxyguanosine 5'-triphosphate and Taq polymerase (34,35,38).

In a further embodiment, the present invention provides a method of detecting the presence of a serotype of infectious bronchitis virus comprising ascertaining the presence of a nucleotide sequence associated with a restriction endonuclease cleavage site, created by digestion with XcmI, by selective amplification by the methods described above.

In yet another embodiment, the present invention provides a method of detecting the presence of a serotype of infectious bronchitis virus comprising ascertaining the presence of a nucleotide sequence associated with a restriction endonuclease cleavage site, created by digestion with XcmI, by hybridizing the sequence with a selective nucleic acid probe. Furthermore, the nucleotide sequence could be amplified prior to hybridization by the methods described above (37).

In a further embodiment, this invention provides a method of detecting the presence of a serotype of infectious bronchitis virus comprising ascertaining the presence of a nucleotide sequence associated with a restriction endonuclease cleavage site, created by digestion with XcmI, by determining the order of nucleotides by sequencing by the methods described above (34,35,38).

Another embodiment of this invention provides a method of detecting the presence of a serotype of infectious bronchitis virus comprising ascertaining the presence of a nucleotide sequence associated with a restriction endonuclease cleavage site, created by digestion with BstYI, by selective amplification by the methods described above.

A further embodiment of the present invention provides a method of detecting the presence of a serotype of infectious bronchitis virus comprising ascertaining the presence of a nucleotide sequence associated with a restriction endonuclease cleavage site, created by digestion with BstYI, by hybridizing the sequence with a selective nucleic acid probe. Furthermore, the nucleotide sequence could be amplified prior to hybridization by the methods described above (37).

Another separate embodiment of this invention provides a polypeptide portion of the S1 protein of infectious bronchitis virus comprising the amino acids encoded by the nucleotide sequence associated with the HaeIII restriction site. These amino acids can be determined by the location of the various restriction sites as described above. In addition, the amino acids could correlate to the polypeptide portion of the S1 protein of IBV comprising the amino acids encoded by the nucleotide sequence associated with the XcmI restriction site. The amino acids could further correlate to the polypeptide portion of the S1 protein of IBV comprising the amino acids encoded by the nucleotide sequence associated with the BstYI restriction site. Additionally, the amino acids could further correlate to the polypeptide portions of the S1 protein of IBV comprising the amino acids encoded by the nucleotide sequences associated with cleavage at two of the three or all three of the BstYI, HaeIII and XcmI restriction sites.

One skilled in the art will appreciate that the restriction enzyme fragments themselves may have immunogenic effect. Thus, any one of the polypeptides encoded by the restriction enzyme fragments could be placed in phosphate buffered saline carrier and injected to elicit an immune response. In this manner, a practitioner could produce vaccines using certain of the restriction enzyme fragments from HaeIII, XcmI, and BstYI cleavage sites.

In addition, one skilled in the art will appreciate that the three restriction enzymes noted in the present invention could be substituted with any three restriction enzymes which cleaved the identical restriction in the same manner. Furthermore, the methods of this invention are readily usable to differentiate additional serotypes of IBV as those serotypes come to be known in the art.

Figure 3:
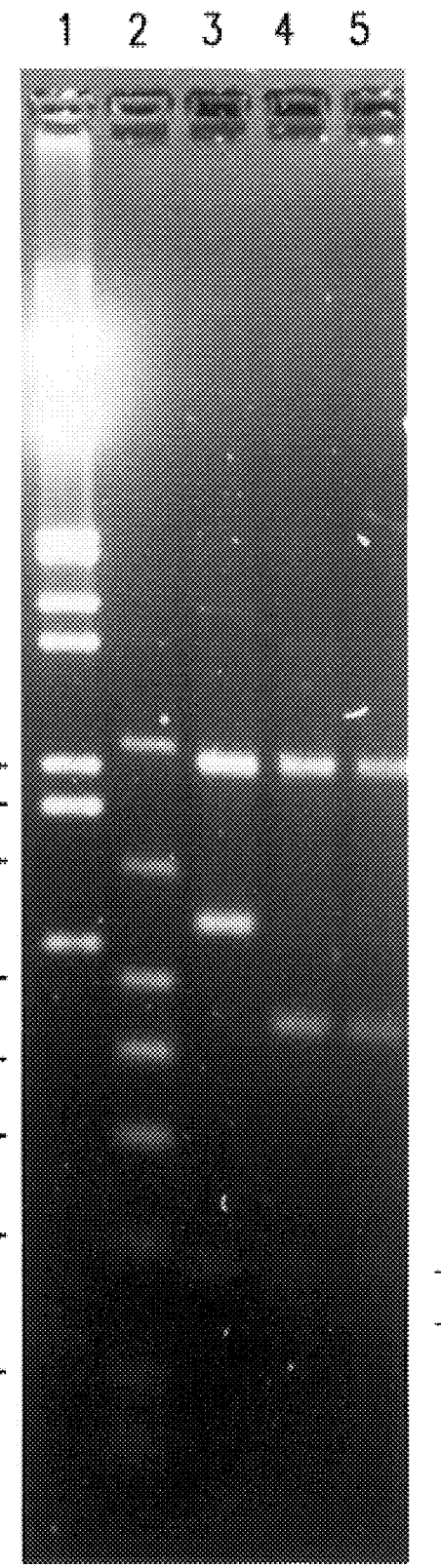
FIG. 3 shows restriction fragment length polymorphism patterns of the PCR amplified S1 glycoprotein genes from IBV Beaudette, Connecticut and Florida strains digested with XcmI. Lane 1; molecular size marker bacteriophage lambda DNA digested with HindIII and EcoRI; lane 2: BioMarker; lane 3: Beaudette strain; lane 4: Connecticut strain; lane 5: Florida strain. Numbers on the vertical axis represent sizes in kilobase pairs of molecular size markers.
Figure 4:
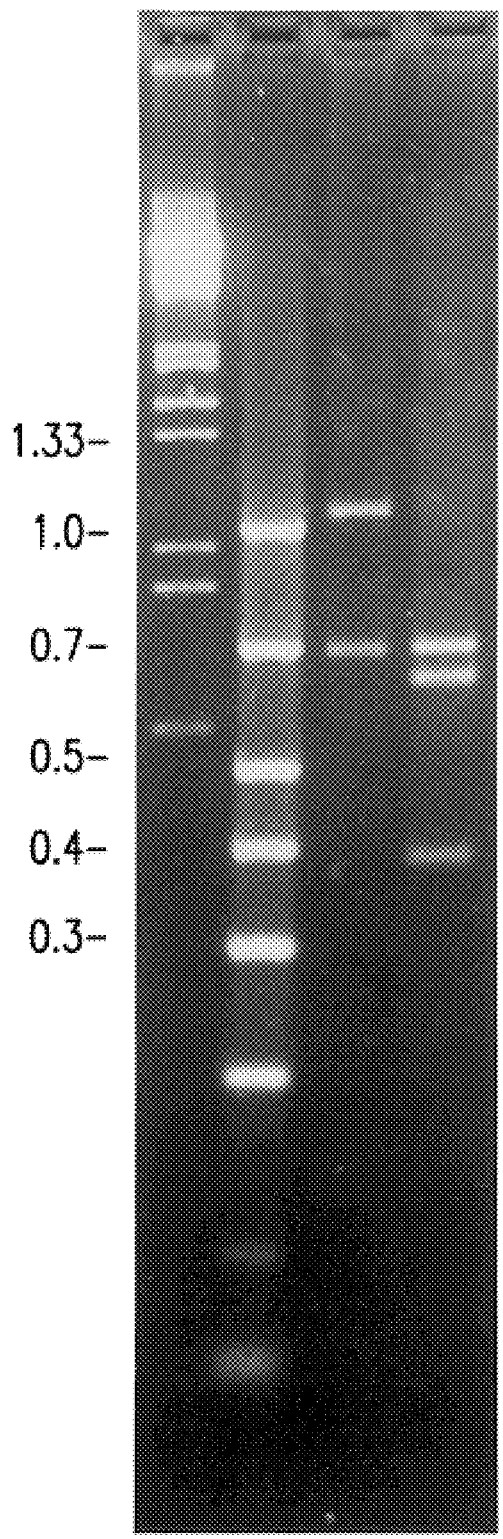
FIG. 4 shows restriction fragment length polymorphism patterns of the PCR amplified S1 glycoprotein genes from IBV Connecticut and Florida strains digested with BstYI. Lane 1: molecular size marker bacteriophage lambda DNA digested with HindIII and EcoRI; lane 2: Biomarker; lane 3: Connecticut; lane 4: Florida strain. Numbers on the vertical axis represent sizes in kilobase pairs of molecular size markers.
Figure 5:
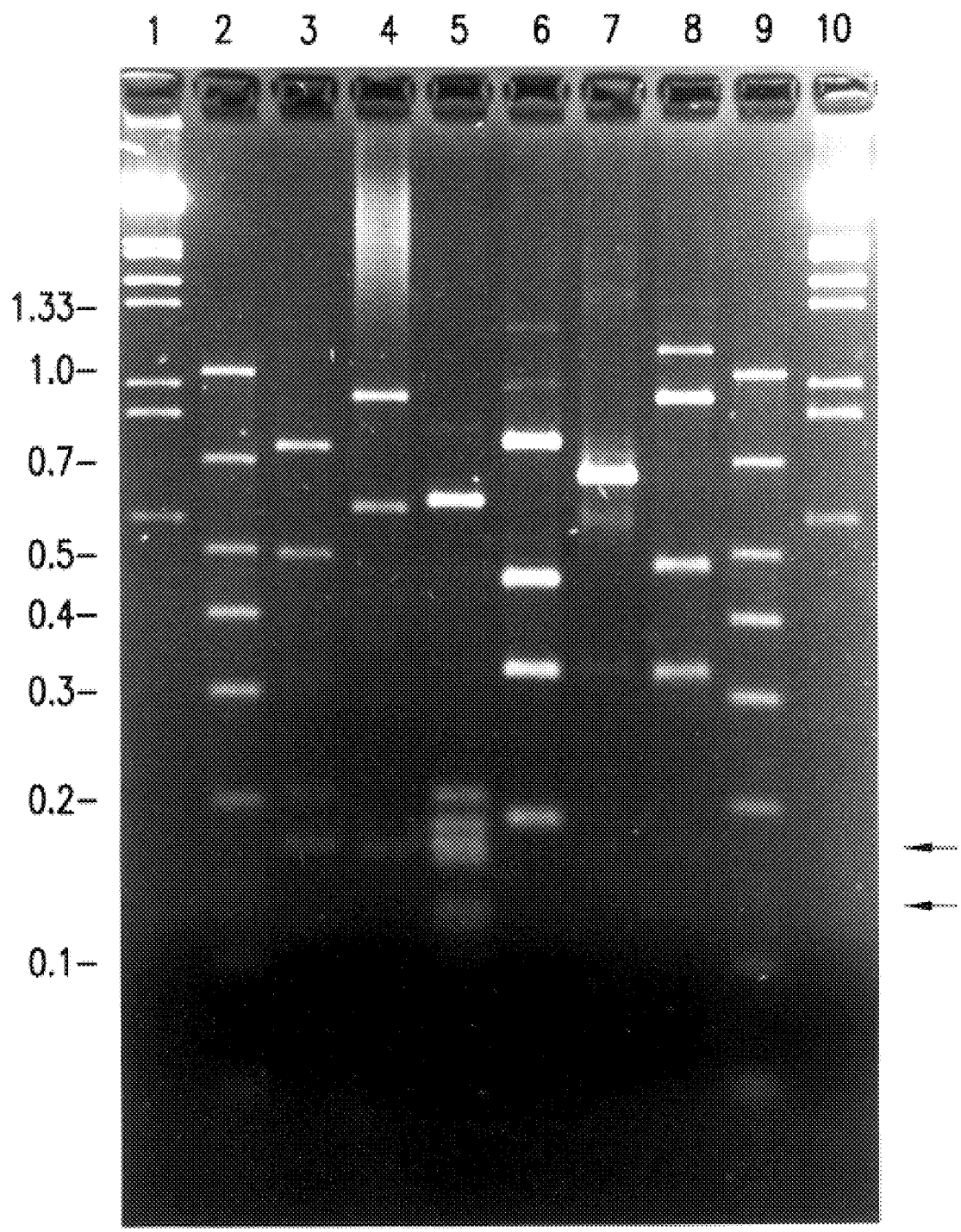
FIG. 5 shows restriction fragment length polymorphism patterns of the PCR amplified S1 glycoprotein genes from IBV variant strains and mixed culture digested with HaeIII. Lane 1 and 10: molecular size marker bacteriophage lambda DNA digested with HindIII and EcoRI; lane 2 and 9: BioMarker; lane 3: 37 (MI); lane 4: 46 C; lane 5: 33 VT; lane 6: 3330; lane 7: 16 VT; lane 8: mixed culture (IBV Massachusetts and Arkansas serotypes). Numbers on the vertical axis represent sizes in kilobase pairs of molecular size markers. The arrows indicate two bands at the bottom of lane 8.

In another embodiment, this invention provides the restriction length polymorphism patterns respectively shown in FIGS. 2–5. Specifically, lanes 3–11 of FIG. 2, lanes 3–5 of FIG. 3, lanes 3 and 4 of FIG. 4, and lanes 3–8 of FIG. 5 represent the relevant patterns for determining IBV serotype. These patterns can be those for the individual restriction enzymes, but in a preferred embodiment the fragments cleaved by all three enzymes (HaeIII, BstYI, XcmI) are run side by side.

The present invention is described in further detail in the following non-limiting examples.

EXAMPLES

Viruses

Eleven different reference IBV strains (7 different serotypes) were used in this experiment, and are listed in Table 1. The viruses were propagated in specific pathogen free (SPF) 10-day old embryonating chicken eggs (SPAFAS, Inc., Norwich, Conn.) as previously described (17).

Twenty-six other IBV samples consisting of field isolates and reference strains (Table 2) of known serotype, by VN testing (10), were assigned a coded number and provided by one of the inventors.

RNA Extraction

Viral RNA was extracted as previously described (25). Briefly, sodium dodecylsulfate (final concentration, 2% wt/vol) and proteinase K (final concentration, 250 µg/ml) were added to allantoic fluid, incubated for 5 minutes at 55 C., then extracted with acid phenol and chloroform/isoamyl alcohol. The RNA was further purified using the RNaid™ kit (BIO 101, La Jolla, Calif.). Finally, the RNA was resuspended in diethyl-pyrocarbonate (DEP)-treated water and stored at −70 C. until used in the reverse transcriptase (RT) reaction.

Polymerase Chain Reaction Oligonucleotide Primers

Primers for the RT reaction and PCR were synthesized by the University of Georgia Molecular Genetics Facility. The primer S10LIG05' consisted of sequence identical to a region near the 5' end of the S1 glycoprotein gene and the primer S10LIG03' consisted of sequence complementary to a region at the 5' end of the S2 glycoprotein gene. Both IBV primers were 20 bases long, and were made with reference to the published sequence for the Beaudette strain of IBV (2). These primers flanked a 1720-base sequence containing the whole S1 glycoprotein gene.

Reverse Transcriptase and Polymerase Chain Reaction

The RT reaction contained 2 µl of 10 x PCR buffer (500 mM KCl, 200 mM Tris HCl, pH 8.4, 0.5 mg/ml nuclease-free bovine serum albumin), 2 µl of 10 mM each dNTP, 250 ng primer S10LIG03', 40 units RNasin (Promega, Madison, Wis.), 1.5 µl of 80 mM MgCl$_2$, and 3 to 6 µl of the RNA solution described above. A 20 µl total reaction volume was obtained by adding sterile DEP-treated water. After heating at 65 C. for 10 minutes, 200 units of Molony murine leukemia virus RT (BRL, Gaitherburg, Md.) was added and the reaction was incubated for 1 hour at 45 C. After incubation, the reaction was stopped by heating to 95 C. for 5 minutes.

For the PCR reaction, 8 µl of 10 x PCR buffer, 250 ng of the S10LIG05' primer, 3.5 µl of 80 mM MgCl$_2$, and 5 units of AmpliTaq DNA polymerase (Perkin-Elmer Cetus, Norwalk, Conn.) were added to the reaction. A 100 µl total reaction volume was obtained by adding sterile distilled water.

The RT reaction and PCR were conducted in a Twin-Block™ thermal cycler (Ericomp, Inc., San Diego, Calif.). The PCR reaction was performed by 35 cycles of denaturation at 94 C. for 1 minute, annealing at 45 C. for 2 minutes, and polymerization at 74 C. for 5 minutes. The initial denaturation and polymerization step were at 94 C. for 5 minutes and at 74 C. for 6 minutes respectively. The final polymerization step was at 74 C. for 10 minutes. The PCR products were analyzed on a 1% agarose gel containing ethidium bromide (0.5 µg/ml) and the amplified DNA was detected using a UV transilluminator.

Restriction Enzyme Analysis

The total PCR reaction product was electrophoresed on a 1% agarose gel (100 V constant voltage). The S1 band with a predicted size of 1720 bp was cut from the gel and purified using the Geneclean kit (BIO 101) according to the manufacturer's recommendations. The purified DNA was equally divided into 3 tubes, and digested with HaeIII (BRL), XcmI, and BstYI (New England Biolabs, Beverly, Mass.) according to the manufacturer's specifications. The restriction fragment patterns were observed following electrophoresis on a 2% agarose gel (100 V constant voltage).

RESULTS

Amplification of the S1 Glycoprotein Gene

The S1 glycoprotein genes of 11 different reference IBV strains were amplified using the S10LIG03' and S10LIG05' primers. The PCR products appeared to be 1720 bp, the predicted size (FIG. 1. Massachusetts 41 and Md 27 are not shown).

Restriction Enzyme Analysis

Following the analysis of RFLP patterns of S1 products obtained with several restriction enzymes (RE), three RE that differentiated the reference IBV strains were selected. The RFLP patterns generated by digestion with HaeIII, XcmI, and BstYI are shown in FIGS. 3, 4, and 5 respectively.

Figure 2:
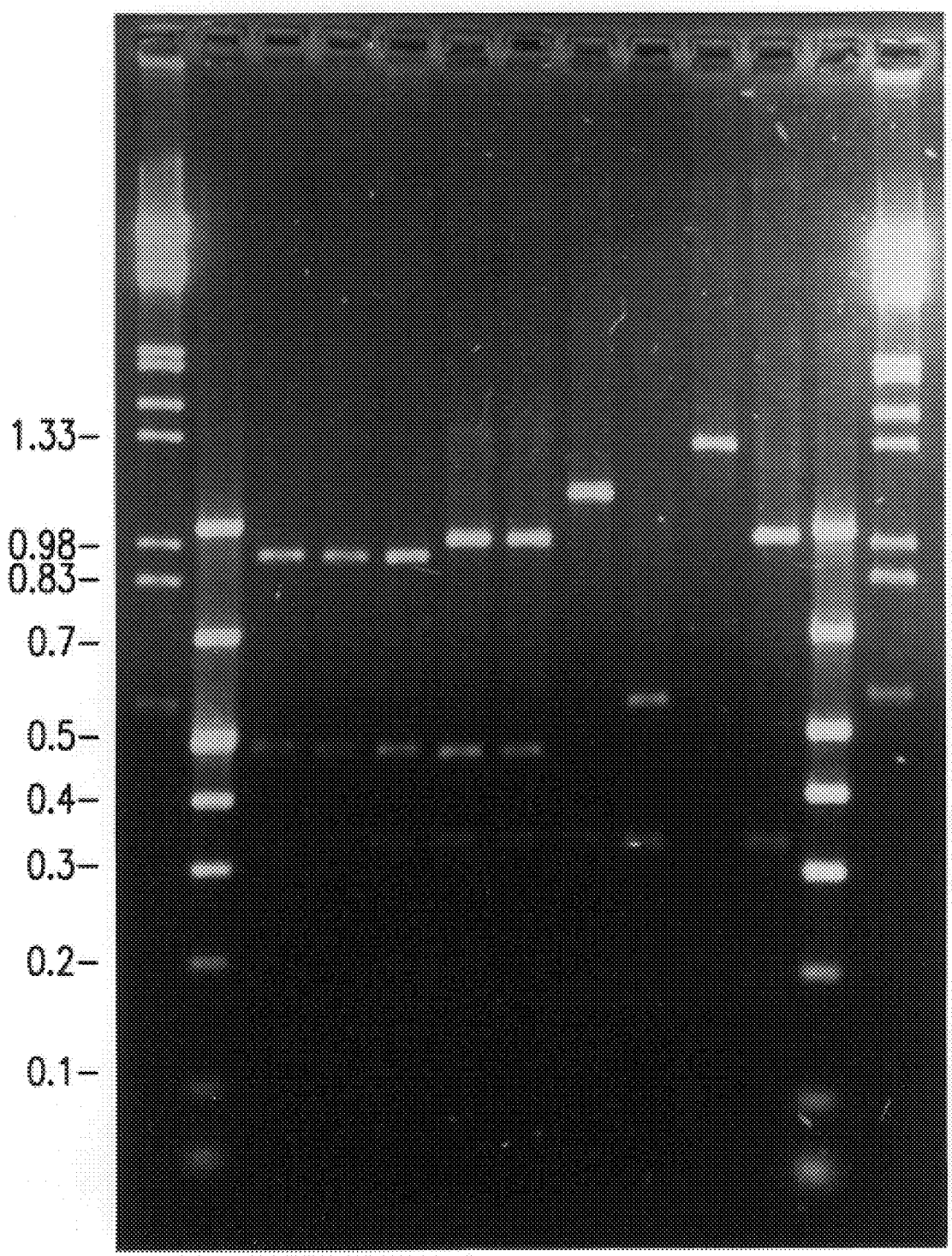
FIG. 2 shows restriction fragment length polymorphism patterns of the PCR amplified S1 glycoprotein genes from several IBV strains digested with HaeIII. Lane 1 and 13: molecular size marker bacteriophage lambda DNA digested with HindIII and EcoRI; lane 2: and 12: molecular size marker BioMarker (BioVenture, Inc., Murfreesboro, Tenn.); lane 3: Beaudette; lane 4: Connecticut; lane 5: Florida; lane 6: Gray; lane 7: JMK: lane 8: Arkansas; lane 9: Holte strain; lane 10: SE 17; lane 11: Iowa 97 strain. Numbers on the vertical axis represent sizes in kilobase pairs of molecular size markers.

The reference strains were grouped according to their RFLP pattern. The Holte, Arkansas, SE 17, and Iowa 97 strains were differentiated from the other IBV strains using HaeIII (FIG. 2). The Beaudette, Connecticut, and Florida strains had the same RFLP pattern, which was different from the RFLP pattern observed for the Gray and JMK strains. The Beaudette strain could be differentiated from the Connecticut and Florida strains by digestion with XcmI (FIG. 3), and the Connecticut and Florida strains could be differentiated by digestion with BstYI (FIG. 4). The Gray and the JMK strains could not be differentiated by any of the RE tested (AciI, AvuII, BsaAI, BsmAI, BspMI, DdeI, DraI, DraIII, DrdI, FokI, HaeII, HpaI, MscI, NarI, NdeI, NlaIV, PstI, PvuII, SphI, SspI). For each of the RE used, the RFLP patterns of the Massachusetts 41 (M41) strain were identical to the RFLP patterns for the Beaudette strain (both Massachusetts serotypes), and the RFLP patterns of the Md 27 strain were identical to the patterns for the SE 17 strain (both Georgia serotypes, data not shown).

Identification of Known Serotypes

To verify the utility and application of this PCR and RFLP serotyping method, we analyzed 26 known samples consisting of field isolates and reference strains of IBV previously serotyped using the VN test in a blind study. Allantoic fluid containing each virus was assigned a number code (from 1–26) and submitted to our laboratory (Department of Avian Medicine, University of Georgia) by Dr. Jack Gelb, Jr. (Department of Agricultural Science and Agricultural Biochemistry, University of Delaware). Serotype identification by the PCR and RFLP analysis agreed with the previously determined serotype of each isolate (Table 2). The RFLP patterns of variant strains did not match the patterns of the reference strains (FIG. 5). The size of the amplification product for virus sample number 23 was smaller (approximately 800 bp) than the predicted size of 1720 bp. That virus was identified as IBV using a previously described PCR based diagnostic test developed in our laboratory (17,25). Virus sample number 26 was not amplified with the S10LIG03' and S10LIG05' primers but was also confirmed as IBV using that previously described PCR diagnostic test. IBV was not detected in virus sample number 27 which was identified as Newcastle disease virus. In sample number 2, which had been serotyped by the VN as Arkansas strain, both Massachusetts and Arkansas serotypes were identified by PCR and RFLP analysis (FIG. 5, lane 8).

Currently, the procedure can be completed in less than two days barring any complications in amplifying the viral genome. The results of PCR and RFLP analysis were consistent with the currently recognized serological classification of IBV (8,14). Moreover, the PCR and RFLP analysis could differentiate some of the IBV isolates within a serotype.

The utility of the PCR and RFLP typing method, was assessed by blindly testing 26 previously serotyped IBV samples consisting of field isolates and reference strains. The classification by PCR and RFLP analysis agreed with the VN serotype for each IBV sample. Variant IBV isolates were also examined by PCR and RFLP analysis and did not match the RFLP patterns of any reference IBV strain. All of the variant strains were confirmed as IBV by the detection method previously described by our laboratory (17,25).

Two different IBV serotypes, Massachusetts and Arkansas, were identified in sample number 2 which had been serotyped as Arkansas. It is noteworthy that different IBV serotypes can be detected in a the mixed culture by PCR and RFLP analysis. An 800 bp amplification product, instead of the 1720 bp product, was detected for sample number 23 which was determined to be a variant virus. Likely explanations for that smaller amplification product are, nonspecific primer annealing, or the S1 gene of that virus was truncated or because it was from a defective-interfering particle (28).

While the foregoing invention has been described in some detail for purposes of clarity and understanding, it will be appreciated by one skilled in the art from a reading of this disclosure that various changes in form and detail can be made without departing from the true scope of the invention and appended claims.

REFERENCES

All publications mentioned hereinabove and fully cited hereinbelow are hereby incorporated by reference.

1. Beaudette, F. R., and C. B. Hudson. Cultivation of the virus of infectious bronchitis. J. Amer. Vet. Med. Assoc. 90:51–60. 1937.
2. Binns, M. M., M. G. Boursnell, D. Cavanagh, D. J. C. Pappin, and T. D. K. Brown. Cloning and sequencing of the gene encoding the spike protein of the coronavirus IBV. J. Gen. Virol. 66:719–726. 1985.
3. Binns, M. M., M. E. G. Boursnell, F. M. Tomley, and T. D. K. Brown. Comparison of the spike precursor sequences of coronavirus IBV strains M41 and 6/82 with that of IBV Beaudette. J. Gen. Virol. 67:2825–2831. 1986.
4. Cavanagh, D. Coronavirus IBV: further evidence that the surface projections are associated with two glycopolypeptides. J. Gen. Virol. 64:1787–1791. 1983.
5. Cavanagh, D., P. J. Davis, J. H. Darbyshire, and R. W. Peters. Coronavirus IBV: virus retaining spike glycopolypeptide S2 but not S1 is unable to induce virus-neutralizing or hemagglutination-inhibiting antibody, or induce chicken tracheal protection. J. Gen. Virol. 67:1435–1442. 1986.
6. Clewley, J. P., J. Morser, R. J. Avery, and B. Lomniczi. Oligonucleotide fingerprinting of ribonucleic acids of infectious bronchitis virus strains. Infect. Immun. 32:1277–1233. 1981.
7. Cook, J. K. A., A. J. Brown, and C. D. Bracewell. Comparison of the hemagglutination inhibition test and the serum neutralization test tracheal organ cultures for typing infectious bronchitis virus strains. Avian Patho. 16:505–511. 1987.
8. Cowen, B. S., and S. B. Hitchner. Serotyping of avian infectious bronchitis viruses by the virus-neutralization test. Avian Dis. 19:583–595. 1975.
9. Darbyshire, J. H., J. G. Rowell, J. K. A. Cook, and R. W. Peters. Taxonomic studies on strains of avian infectious bronchitis virus using neutralization tests in tracheal organ cultures. Arch. Virol. 61:227–238. 1979.
10. Gelb, J. Jr., B. E. Perkins, J. K. Rosenberger, and P. H. Allen. Serologic and cross-protection studies with several infectious bronchitis virus isolates from Delmarva-reared broiler chickens. Avian Dis. 25:655–666. 1981.
11. Gelb, J. Jr. Infectious bronchitis In: A laboratory manual for the isolation and identification of avian pathogens, 3rd ed. H. G. Purchase, L. H. Arp, C. H. Domemuth, and J. E. Pearson, eds. American Association of Avian Pathologists, Kennett Square, Pa. pp. 124–127. 1989.
12. Gelb, J. Jr., J. B. Wolff, and C. A. Moran. Variant serotypes of infectious bronchitis virus isolated from commercial layer and broiler chickens. Avian Dis. 35:82–87. 1991.
13. Hofstad, M. S. Antigenic differences among isolates of avian infectious bronchitis virus. Am. J. Vet. Res. 19:740–743. 1958.
14. Hofstad, M. S. Cross-immunity in chickens using seven isolates of avian infectious bronchitis virus. Avian Dis. 25:650–654. 1981.
15. Hopkins, S. R. Serologic and immunologic properties of a recent isolate of infectious bronchitis virus. Avian Dis. 13:356–362. 1969.
16. Hopkins, S. R. Serological comparison of strains of infectious bronchitis virus using plaque-purified isolants. Avian Dis. 18:231–239. 1974.
17. Jackwood, M. W., H. M. Kwon, and D. A. Hilt. Infectious bronchitis virus detection in allantoic fluid using the polymerase chain reaction and a DNA probe. Avian Dis. 36:403–409. 1992.
18. Jungherr, E. L., T. W. Chomiak, and R. E. Luginbuhl. Immunologic differences in strains of Infectious bronchitis virus. Proceeding of the 60th Annu. Meeting of the U.S. Livestock Sanitary Assoc. pp. 203–209. 1956.
19. King, D. J., and S. R. Hopkins. Rapid serotyping of infectious bronchitis virus isolates with the hemagglutination-inhibition test. Avian Dis. 28:727–733. 1984.
20. King, D. J. Identification of recent Infectious bronchitis virus isolates that are serologically different from current vaccine strains. Avian Dis. 32:362–364. 1988.

21. King, D. J., and D. Cavanagh. Infectious bronchitis. In: Diseases of poultry, 9th ed. B. W. Calnek, H, J. Barnes, C. W. Beard, W. M. Reid, and H. W. Yoder Jr., eds. Iowa State University Press, Ames, Iowa. pp. 471–484. 1991.

22. Koch, G., L. Hartog, A. Kant, D. van Roozelaar, and G. F. de Boer. Antigenic differentiation of avian bronchitis virus variant strains employing monoclonal antibodies. Isr. J. Vet. Med.42:89–97. 1986.

23. Koch, G., L. Hartog, A. Kant, and D. J. van Roozelaar. Antigenic domains of the peplomer protein of avian infectious bronchitis virus: correlation with biological functions. J. Gen. Virol. 71:1929–1935. 1990.

24. Kusters, J. G., H. G. M. Niesters, J. A. Lenstra, M. C. Horzinek, and B. A. M. van der Zeijst. Phylogeny of antigenic variants of avian coronavirus IBV. Virology. 169:217–221. 1989.

25. Kwon, H. M., M. W. Jackwood, T. P. Brown, and D. A. Hilt. The polymerase chain reaction and a biotin labeled DNA probe for detection of infectious bronchitis virus in chickens. Submitted to Avian Dis.

26. Lin, Z., A. Kato, Y. Kudou, and S, Ueda. A new typing method for the avian infectious bronchitis virus using polymerase chain reaction and restriction enzyme fragment length polymorphism. Arch. Virol. 116:19–31. 1991.

27. Lin, Z., A. Kato, Y. Kudou, K. Umeda, and S. Ueda. Typing of recent infectious bronchitis virus isolates causing nephritis in chicken. Arch. Virol. 120:145–149. 1991.

28. Makino, S., C-K. Shieh, J. G. Keck, and M. C. Lai. Defective-interfering particles of murine coronavirus: mechanism of synthesis of defective viral RNAS. Virology 163:104–111. 1988.

29. Saiki, R. K., D. H. Gelfand, S. Stoffel, S. J. Scharf, R. Higuchi, G. T. Horn, K. B. Mullis, H. A. Erlich. Primer-directed enzymatic amplification of DNA with a thermostable DNA polymerase. Science 239:487–491. 1988.

30. Siddle, S., H. Wege, and V. ter Meulen. The structure and replication of coronaviruses. Curr. Top. Microbiol. Immunol. 99:131–163. 1982.

31. Winterfield, R. W., and S. B. Hitchner. Etiology of an infectious nephritis-nephrosis syndrome of chickens. Am. J. Vet. Res. 23:1273–1279. 1962.

32. Winterfield, R. W., S. B. Hitchner, and G. S. Appleton. Immunological characteristics of a variant of infectious bronchitis virus isolated from chickens. Avian Dis. 8:40–47. 1964.

33. Winterfield, R. W., A. M. Fadly, and J. E. Hanley. Characterization of an isolate of infectious bronchitis virus from chickens in Florida. Avian Dis. 15:305–311. 1971.

34. Shoffner, J. M., M. T. Lott, A. S. Voljavec, S. A. Soueidan, D. A. Costigan, D. C. Wallace. Spontaneous Kearns-Sayre/chronic external opthalmoplegia plus syndrome associated with a mitochondrial DNA deletion: A slip-replication model and metabolic therapy. Proc. Natl. Acad. Sci. USA 86:7952–7956. 1989.

35. Innis, M. A., K. B. Myambo, D. H. Gelfand, M. D. Brow. DNA sequencing with Thermus aquaticus DNA polymerase and direct sequencing of polymerase chain reaction-amplified DNA. Proc. Natl. Acad. Sci. USA 85:9436–9440. 1988.

36. Sambrook, J., E. F. Fritsch, T. Maniatis. Molecular Cloning, A Laboratory Manual, 2d Ed. Cold Spring Harbor Laboratory Press, Cold Spring Harbor, N.Y. 1989.

37. Kwoh, Debra Y., T. Jesse Kwoh. Target amplification systems in nucleic acid based diagnostic approaches. American Biotechnology Laboratory 8:14–25. October 1990.

38. Sanger, F., S. Nicklen, A. R. Coulson. DNA sequencing with chain-terminating inhibitors. Proc. Natl. Acad. Sci. USA 74:5463–5467. 1977.

39. Binns, M. M., M. E. G. Boursnell, D. Cavanagh, D. J. C. Pappin and T. D. K. Brown. Cloning and sequencing of the gene encoding the spike protein of the coronavirus IBV. J. Gen. Virol. 66:719–726. 1985.

40. Boursnell, M. E. G., M. M. Binns and T. D. K. Brown. Sequencing of coronavirus IBV genomic RNA: Three open reading frames in the 5' unique region of mRNA D. J. Gen. Virol. 66:2253–2258. 1985.

41. Boursnell, M. E. G., M. M. Binns, I. J. Foulds and T. D. K. Brown. Sequences of the nucleocapsid genes from two strains of avian infectious bronchitis virus. J. Gen. Virol. 66:573–580. 1985.

42. Boursnell, M. E. G. and T. D. K. Brown. Sequencing of coronavirus IBV genomic RNA: A 195-base open reading frame encoded by mRNA B. Gene 29:87–92. 1984.

43. Boursnell, M. E. G., T. D. K. Brown and M. M. Binns. Sequence of the membrane protein gene from avian coronavirus IBV. Virus Res. 1:303–313. 1984.

44. Boursnell, M. E. G., T. D. K. Brown, I. J. Foulds, P. F. Green, F. M. Tomley and M. M. Binns. Completion of the sequence of the genome of the coronavirus avian infectious bronchitis virus. J. Gen. Virol. 68:57–77. 1987.

45. Niesters, H. G. M., J. A. Lenstra, W. J. M. Spaan, A. J. Zijderveld, N. M. C. Bleumink-Pluym, F. Hong, G. J. M. van Scharrenburg, M. C. Horzinek and B. A. M. Van Der Zeijst. The peplomer protein sequence of the M41 strain of coronavirus IBV and its comparison with Beaudette strains. Virus Res. 5:253–263. 1986.

What is claimed is:

1. A method of distinguishing between serotypes and/or detecting variants of infectious bronchitis virus comprising:
   a. amplifying the S1 gene region of infectious bronchitis virus;
   b. digesting the amplified S1 gene region with HaeIII, or a restriction endonuclease which cleaves at the HaeIII restriction site, to form a first set of restriction fragments;
   c. digesting the amplified S1 gene region with XcmI, or a restriction endonuclease which cleaves at the XcmI restriction site, to form a second set of restriction fragments;
   d. digesting the amplified S1 gene region with BstYI, or a restriction endonuclease which cleaves at the BstYI restriction site, to form a third set of restriction fragments;
   e. separating the restriction fragments within the first, second and third sets by electrophoresis; and
   f. analyzing restriction fragment length polymorphisms to distinguish between serotypes or detect variants of infectious bronchitis virus.

2. A primer for amplifying the S1 gene region of infectious bronchitis virus comprising a nucleic acid, having at least 20 nucleotides, which selectively hybridizes between nucleotide positions −100 through +1, relative to the ATG start site of S1, of the negative strand of infectious bronchitis virus.

3. The primer of claim 2, wherein the primer is SEQ ID NO:4 (S10LIG05').

4. A primer for amplifying the S1 gene region of infectious bronchitis virus comprising a nucleic acid, having at least 20 nucleotides, which selectively hybridizes between nucleotide positions 1600 through 1700, relative to the ATG start site of S1, of the positive strand of infectious bronchitis virus.

5. The primer of claim 4, wherein the primer is SEQ ID NO:6 (S10LIG03').

* * * * *